United States Patent [19]

Porsche

[11] Patent Number: 5,768,716
[45] Date of Patent: Jun. 23, 1998

[54] GOGGLES, IN PARTICULAR FOR SPORTS AND/OR LEISURE WEAR

[75] Inventor: Ferdinand A. Porsche, Zell am See, Austria

[73] Assignee: Porsche Design GmbH, Zell am See, Austria

[21] Appl. No.: 637,658
[22] PCT Filed: Sep. 2, 1995
[86] PCT No.: PCT/EP95/03456
§ 371 Date: Jul. 9, 1996
§ 102(e) Date: Jul. 9, 1996
[87] PCT Pub. No.: WO96/07948
PCT Pub. Date: Mar. 14, 1996

[30] Foreign Application Priority Data

Sep. 2, 1994 [DE] Germany .......................... 44 31 328.4

[51] Int. Cl.⁶ ...................................................... A61F 9/02
[52] U.S. Cl. ........................ 2/454; 2/446; 2/448; 351/63
[58] Field of Search ............................... 2/426, 431, 432, 2/446, 447, 448, 450, 453, 454; 351/63, 137, 138, 124, 44, 47, 128

[56] References Cited

U.S. PATENT DOCUMENTS

| | | | |
|---|---|---|---|
| 2,275,999 | 3/1942 | Strauss | 2/454 |
| 2,307,419 | 1/1943 | McNeill et al. | 2/454 |
| 2,443,422 | 6/1948 | Hansen | 2/454 |
| 2,563,125 | 8/1951 | Malcom, Jr. | 2/450 |
| 2,907,041 | 10/1959 | Finn | 2/454 |
| 2,975,426 | 3/1961 | Rabb | 351/63 |
| 3,383,155 | 5/1968 | Bourke | 2/453 |
| 3,395,964 | 8/1968 | Neider | 351/63 |
| 3,944,344 | 3/1976 | Wichers | 351/41 |
| 4,951,322 | 8/1990 | Lin | 2/439 |
| 4,998,815 | 3/1991 | Lin | 2/450 |
| 5,357,292 | 10/1994 | Wiedner | 2/450 |
| 5,379,463 | 1/1995 | Schleger et al. | 2/431 |
| 5,390,369 | 2/1995 | Tubin | 2/448 |
| 5,423,092 | 6/1995 | Kawai | 2/447 |

FOREIGN PATENT DOCUMENTS

| | | | |
|---|---|---|---|
| 457706 | 6/1949 | Canada . | |
| 2085536 | 12/1971 | France . | |
| 2681442 | 3/1993 | France . | |
| 919436 | 10/1954 | Germany | 351/63 |
| 2151809 | 7/1985 | United Kingdom . | |
| 2270994 | 3/1994 | United Kingdom . | |
| WO8900844 | 2/1989 | WIPO . | |
| WO9304392 | 3/1993 | WIPO . | |

Primary Examiner—Amy B. Vanatta
Attorney, Agent, or Firm—Weingarten, Schurgin, Gagnebin & Hayes LLP

[57] ABSTRACT

The invention concerns goggles, in particular for sports and/or leisure wear, having a side piece, a curved front bar, a visor and a bridge for the nose. The side piece and the visor can be pivoted relative to each other. In the operating position they lie in different planes at an angle to each other and, in the rest position, they lie in planes substantially parallel to each other. The visor is resilient and is connected to the side piece by means of hinges or guides disposed in an eccentric or lateral area of the visor such that, when the side piece pivots towards the visor, the latter is resiliently deformed and is adapted to the shape of the front bar. If non-resilient visors are provided, the bridge connecting them is resilient and deformed resiliently when the side piece is pivoted towards the visors. In this way, the visors are moved into the desired operating position.

19 Claims, 9 Drawing Sheets

GOGGLES, IN PARTICULAR FOR SPORTS AND/OR LEISURE WEAR

FIELD OF THE INVENTION

The invention concerns goggles, in particular for sports and/or leisure wear, according to the preamble to the main claim.

BACKGROUND OF THE INVENTION

A pair of goggles with a U-shaped side piece connected to a hinged frame is known from FR 20 85 536. The side piece can be pivoted in relation to the frame with the visor arranged therein in such a way that in the operating position, the side piece and the visor lie in different planes approximately perpendicular to one another, and in the non-operating position, the two parts lie in planes basically parallel to one another. The design of the side piece, its shape and the possibility of adjusting it easily to the shape of the wearer's head and the possibility of padding the goggles and equipping them with other aids that make them more comfortable to wear are given. When the visor is in the operating position, it is arranged on the U-shaped side piece adjacent to the wearer's forehead so it hangs down from a hinge placed in the center of the frame, roughly in the bridge area. This affects not only the aesthetic impression but also the wearing comfort of such goggles due to the projecting frame.

GB 15 30 691 describes goggles in which the visor is in a plane staggered 90 degrees to the plane of the side piece in the operating position, and when not in use, swings up, i.e., away from the nose in such a way that it forms an extension of the goggle plane. Such arrangements have been known for a long time, and the design is similar to the mirror a physician wears on his head.

DE OS 34 131 72 describes another pair of goggles, in which an extra visor can pivot opposite the frame in which corrective lenses are arranged and can be stopped in the pivoted position. The pivoting movement is made, for the most part, away from the nose, i.e., toward the upper part of the side piece. Here the visor and the side piece are in two different planes, regardless of whether the goggles are in the operating or non-operating position.

DE OS 34 39 830 also describes goggles with a removable visor, in which a changeable visor is used on a curved side piece and attached to the side piece near the bridge. But the structural form of the glasses described here does not allow the goggles to pivot toward the side piece.

SUMMARY OF THE INVENTION

The task of this invention is to specify goggles with small dimensions in the non-operating position, especially small height, with optimal wearing comfort. The goggles should also be aesthetically pleasing.

This task is solved by the goggles specified in claims 1 and 16. The subclaims introduce advantageous variations.

The special design of the goggles, especially the flexing of the ear piece toward the front piece and the pivoting of the side piece into the plane of the visor, guarantee an aesthetically pleasing impression and maximum wearing comfort. This is particularly due to the fact that the goggles have means that not just allow the side piece to pivot in relation to the visor or visors, but, due to their special arrangement and design, allow the resilient visor to be pulled and adjusted to the curvature, i.e., to the shape of the front piece. Here, the principle of a simple, very light goggle design, wherein the visor is preferably frameless is not abandoned. By making the side piece so it can fold away from the bridge and the visors or visors in the plane of the side piece or in a plane extending basically parallel to it, in the non-operating position, the height of the goggles in the invention is only roughly the thickness of the side piece plus the visor, which is only roughly 8–9 mm. The plane of the visor in one advantageous embodiment may lie basically in the plane of the side pieces. In this case, when the goggles are in the non-operating position, the side piece with its two sections, the front piece and the ear pieces, is flat on the visor or visor sections. When the goggles are in the operating position, optimal wearing comfort is guaranteed, i.e., the curved shape of the goggles is fully guaranteed due to the curve of the visor which follows the curve of the front piece, which is important especially for sports and/or leisure wear.

At the same time, the simple form of embodiment of the goggles in the invention, which is advantageous to use, makes positioning the visor secure in relation to the side piece. This positioning can be done either by a separate means of positioning or by guides for the front piece arranged on the visor.

The visor or visor sections are connected to one another independently of the side pieces. In this way, they can be connected by a nose pad or a one-piece visor.

When not in use, the visor can be brought into the plane of the side piece or, in one advantageous embodiment, into a plane basically parallel to the plane of the side piece by the deformation of an elastic element. The elastic element is deformed by the pivoting movement of the side piece. Depending on the pivoting movement and the respective pivoting position of the side piece, it can be deformed against it, i.e., the deformation of the elastic element can be influenced by the pivoting position of the side piece. The elastic element is formed by an elastically deformable visor or visor sections, or by an elastically deformable bridge for the nose. The visor or visor sections or a one-piece visor follow the pivoting movement of the side piece or the curved front piece insofar as they adjust to the curvature of the front piece because of their elasticity, on one hand, and because of the fixed pivoting connection between them and the side piece. The visor sections can go into one another forming a nose bridge area, so that they form a one-piece visor. An elastic material is suitable for the design of this visor, preferably a polycarbonate with a hardcore coating, which guarantees scratch-resistance inside and out. If the visor is in one piece, the bridge has stiffening, which compensates for the lability of the visor in this area due to the nose cutout and gives the visor approximately the stiffness and elasticity of a disk with constant dimensions. The fixed connection between the visor or visor sections and the side piece is designed as a joint or guide. The jointed connection, which allows the side piece to pivot in relation to the visor or visor sections, is preferably designed as a hinged connection. In this way, the hinges can be arranged either on the visor, preferably as loops that go around the side piece, or as hinges in the front piece. The goggles in the invention also have means of positioning, which make it possible to position the front piece against the visor or visor sections. In one form of embodiment, they are formed by a snap connection between the visor or visor sections and the front piece. For this, the front piece has a projection which goes into a recess on the visor. Here, provision is made for stops to be arranged in the area of the hinges on the front piece, which are positioned in relation to the visor or visor sections during the pivoting movement so that the snap projection fits securely into a corresponding recess on the visor. Another form of embodiment of the invention provides for guides to be arranged on the outer edge of the visor or visor sections into which the front piece fits during its pivoting movement, so it can be positioned in the operating position of the goggles by interlocking and spring-action. The front piece is also connected to the visor by a pivot connection arranged in the middle. If the side guides are designed so that they have the form of endpieces with a straight guide for the front piece, then a pivoting connection in the form of a hinge is provided in the middle of the visor; this hinge works with the side guides so that the visor is deformed by pivoting the front piece.

It is especially advantageous if the pivoting connection is designed to be removable. This form of embodiment makes it possible for various visors or visor sections to be used on the same side piece. For this, the pivot connection can be designed so that the loops that go around the side piece are not completely closed and release the side piece when turned 90 degrees. A closed form of embodiment of the loops also provides that they be connected to the visor. Another variation provides for a hook-shaped element that goes through the visor to go around the side piece and for the side piece to come out of the hook-shaped element, when necessary, by the yielding of an elastic element. Finally, the connection between the front piece and the hinge can be designed as a snap-on connection.

It is especially advantageous if the side piece is composed of a wire-shaped material made of a nickel-free alloy or a plastic-coated metal core. The side-piece material has a stiffness essential to the design and is springy at high stresses.

BRIEF DESCRIPTION OF THE DRAWING

The invention will be described in greater detail below using examples of embodiment shown in the drawings.

DETAILED DESCRIPTION OF THE DRAWING

Figure 7:
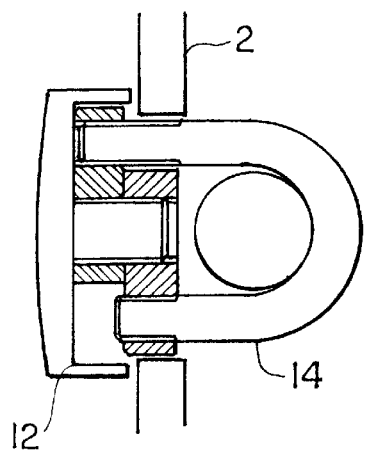
FIG. 7 shows a form of embodiment of the removable pivot connection.
Figure 8:
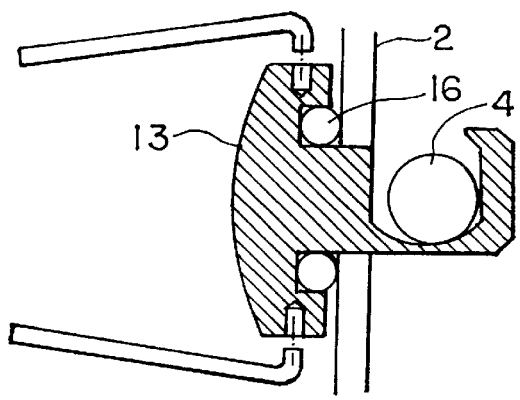
FIG. 8 shows another form of embodiment of the removable pivot connection.

The goggles in the invention have a side piece 3, with a curved front piece 4 and ear pieces 5 and a bridge 7 for the nose in a visor 2 which may include visor sections 1, which can be one-piece according to the form of embodiment shown in FIGS. 1 to 5 and 11 to 14. The side piece 3 is connected to the lenses 1 or a one-piece visor 2 by a joint connection 8 in the area of the front piece 4. The front piece 4 is connected to the ear pieces 5 via hinges 9, preferably via built-in hinges, like for example spring hinges. The ear pieces 5 have the usual earpiece supports 10, which can also be designed as plastic supports 23. The jointed connection 8 between the side piece 3 and front piece 4 and the lenses 1 or one-piece visor 2 is designed as a hinge. According to one form of embodiment of the goggles in the invention, which is shown in FIGS. 1 to 4, the joint is made so that a fastening element 11, 12, 13 goes from the outside through the visor 2 and goes around the front piece 4 on the inside with loops 14 or hooks 15. In this way, the loops 14 can open so that they release an area of the side piece 4, or as shown in FIG. 7, closed so that the side piece 4 is entirely in the loop 14. The first form of embodiment has a removable pivot connection between the side piece 3 and the visor 2, wherein the front piece 4 is free when the loops 14 are turned 90 degrees. According to the form of embodiment shown in FIG. 7, the fastening element 12 is screwed out of the visor 2, the closed loop 14 pulled out and the front piece 4 thereby free. In the view in FIG. 8, the hook 15 is opened and the front piece 4 released by turning the fastening element 13 against an elastic sealing ring 16. Due to the fact that the pivot connection 8 is removable, the invention makes it possible to change the overall aesthetic look of the goggles with another visor, mainly by using lenses 2 that are designed differently aesthetically.

In the forms of embodiment shown in FIGS. 1 to 4 of the goggles in the invention, two joint connections 8 are provided which are arranged in the outer central area of the visor 2. The arrangement of two joint connections 8 not only guarantees the connection between the side piece 3 and the visor 2 will work, but no other means is necessary to adjust the curvature of it or of the front piece 4 when the goggles 3 are pivoted or tipped against the visor 2. To make the curvature of the visor 2 large enough on its outer areas, the front piece 4 can have offsets in that area. For the working of the goggles in the invention, it is important that there be an elastic element, which is adjusted to the curvature of the front piece 4 when the side piece is pivoted. The visor 2 is elastic and preferably composed of coated polycarbonate. In the form of embodiment in FIGS. 9 and 10, the lenses 1 are not elastic, but they are connected to one another by an elastic bridge 6, whose elasticity and ductility are important to the function of the form of embodiment of the goggles in the invention shown in FIGS. 9 and 10. On the other hand, the bridge 7 in the form of embodiment of the goggles in the invention shown in FIG. 1 only perform the function of connecting two lens sections or represents part of the one-piece visor 2.

Figure 1:
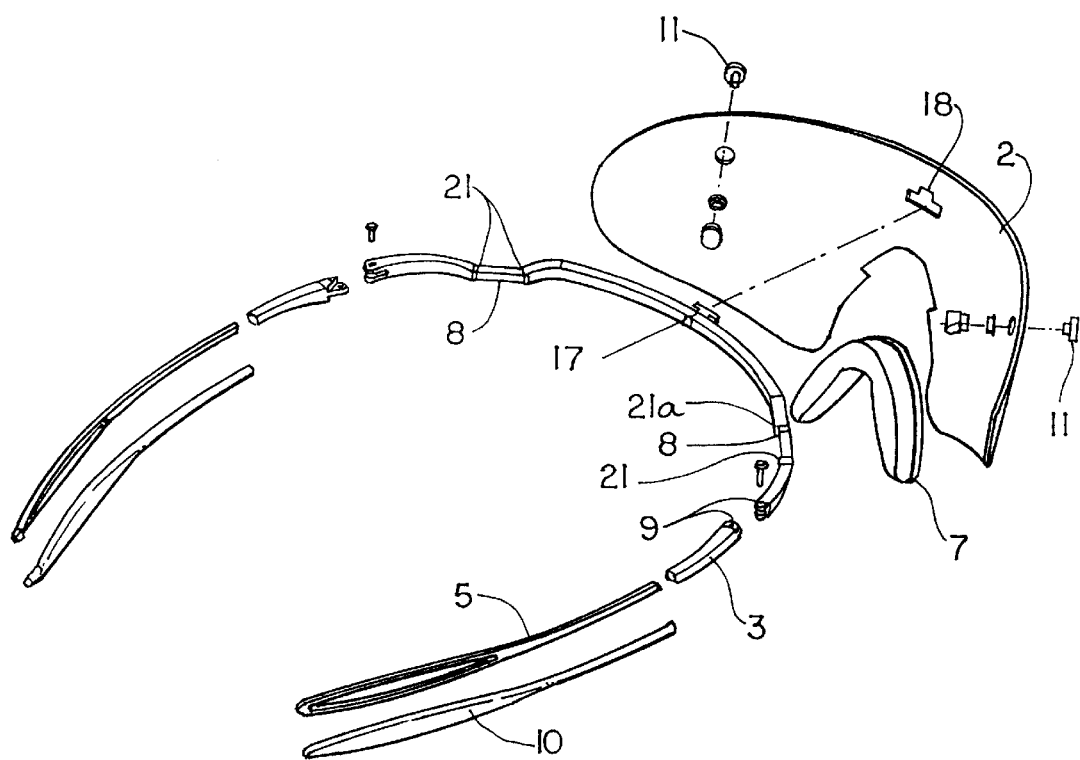
FIG. 1 shows an exploded view of the goggles.
Figure 2:
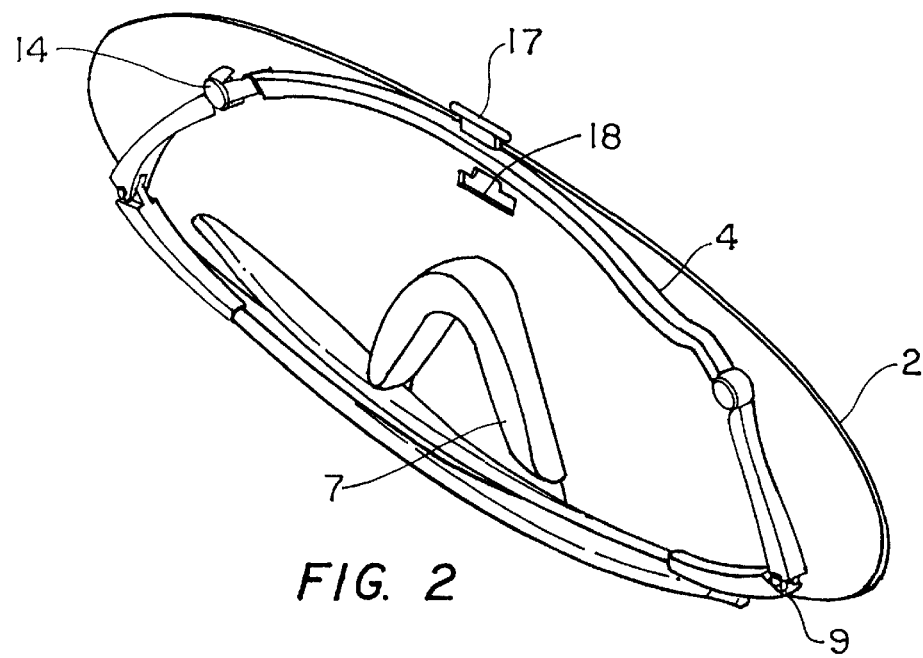
FIG. 2 shows a perspective view of the goggles in the folded position (non-operating position).
Figure 3:
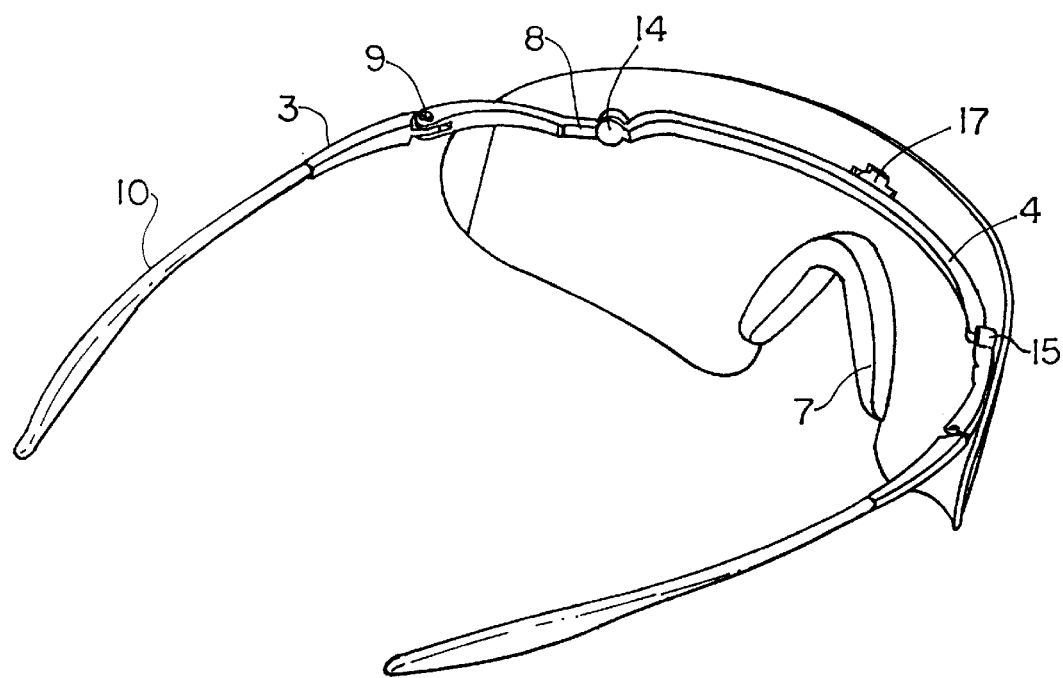
FIG. 3 shows a perspective view of the goggles in the operating position.
Figure 4:
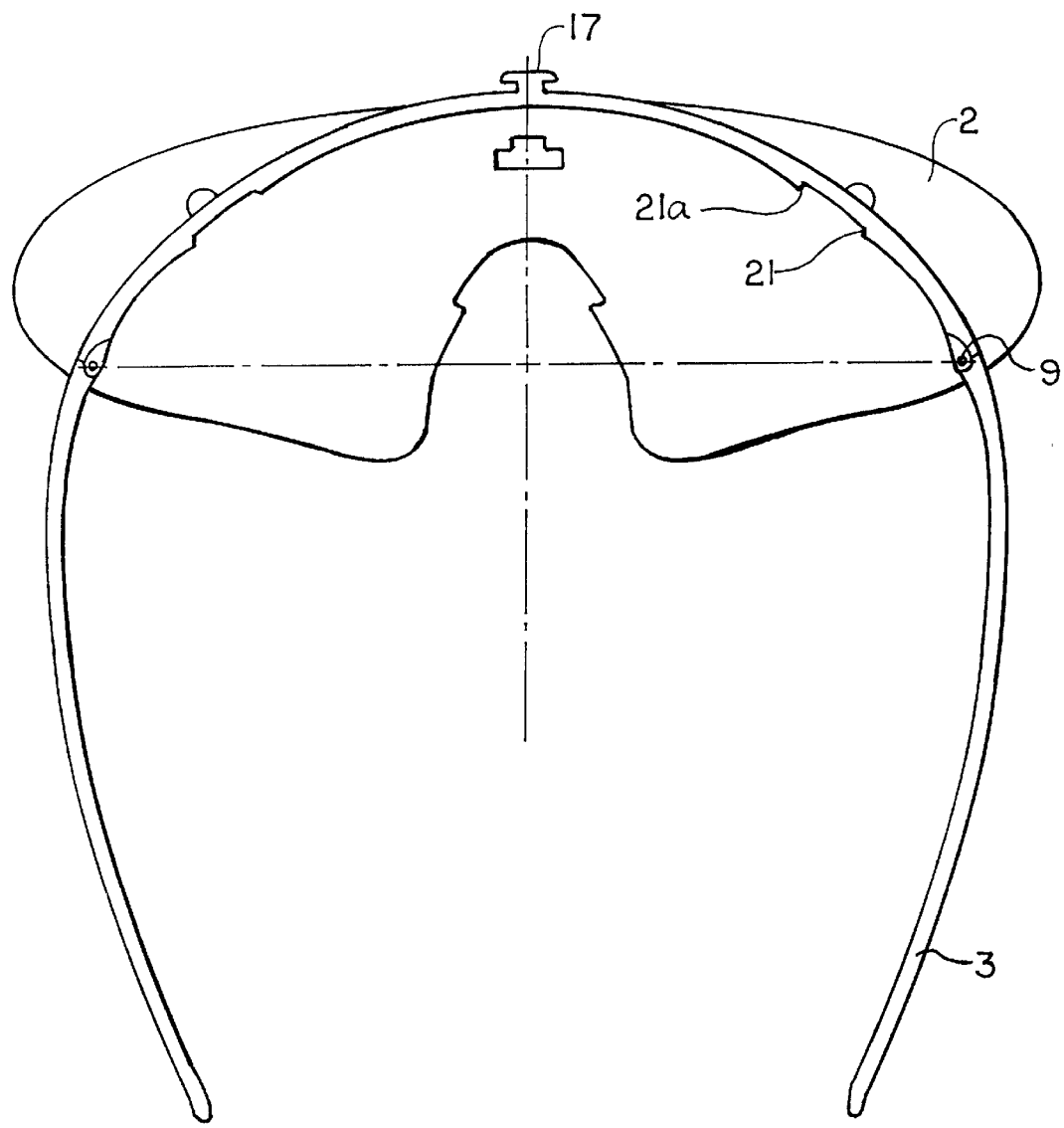
FIG. 4 shows a top view of the goggles with unfolded ear pieces in the non-operating position.
Figure 5:
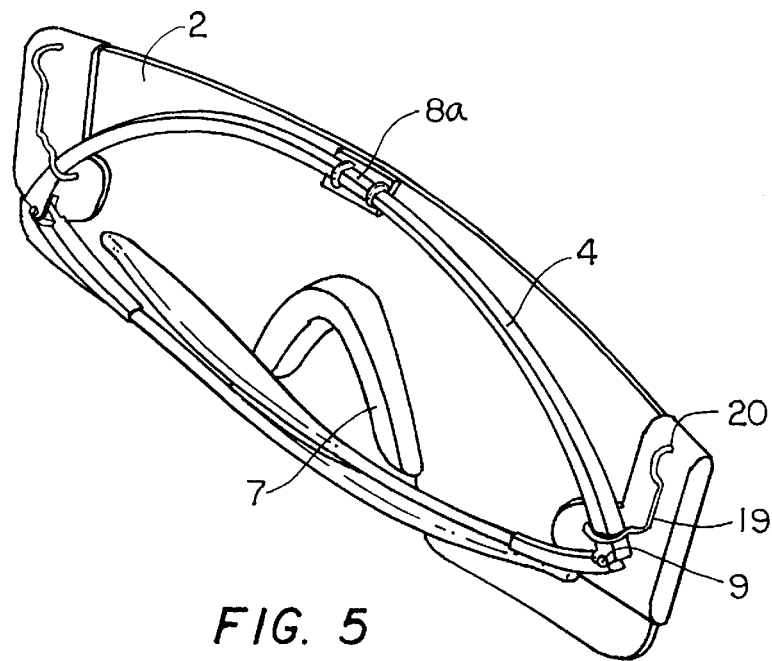
FIG. 5 shows a view of another form of embodiment of the goggles with closed ear pieces in the non-operating position.

The goggles have means of positioning which allow the goggles 3 to be positioned precisely in relation to the visor 2 in their operating and non-operating position. In the form of embodiment shown in FIG. 1, these means are a projection 17 on the front piece 4, which goes into a recess 18 on the visor 2. The means of positioning in the goggles shown in FIG. 5 are designed with guides 19 arranged on the sides of the visor 2 and a pivot connection 8a arranged in the center of the visor. The movement of the front piece 4 is controlled by the guides 19 and in the end position, which corresponds to the operating position of the goggles, is fixed in areas 20 by interlocking and spring-action. The hinge 8a in which the front piece 4 is turned keeps the visor 2 from folding down when the goggles are in the operating position and the side piece from folding down and out in the non-operating position. FIGS. 11 to 14 show the side piece 3 in the lateral, straight guides of the endpieces 24, where there is another hinge 25 in the middle of the visor 2 whereby the front piece 4 is positioned on the visor 2 and in which the turning movement of the front piece 4 takes place. The joint 25 is designed as a double snap-on connection. On one hand, the joint 25 is snapped into the recesses 26 of the visor with its snap projections 27; on the other hand, the front piece 4 is snapped into and held between the snap projections 27 when the joint 25 is attached to the visor 2. At the same time, the joint 25 is held on one side of the visor 2 by its surface 35 and on the other side by the front piece 4.

The front piece 4 has stops 21, 21a, which are arranged in the area of the joint connection 8. These stops 21 are positioning aids. They are arranged on both sides of the connecting element 14, 15, and their distance corresponds to the respective ratio between the curvature of the front piece and the flat visor 2, taking into account a given inclination of it. The stops 21a guarantee that the snap connection, which is formed by the snap projection 17 and the recess 18, is always exact. The stops 21 are decisive for positioning the side piece of the goggles in the non-operating position. The snap projection 17 is rounded on all sides in order to avoid any potential damage to the visor 2. This guarantees that when the side piece 3 is pivoted in relation to the visor 2, the snap projection 17 does not come out of the recess 18 if there is extraordinary stress on the goggles.

Figure 6:
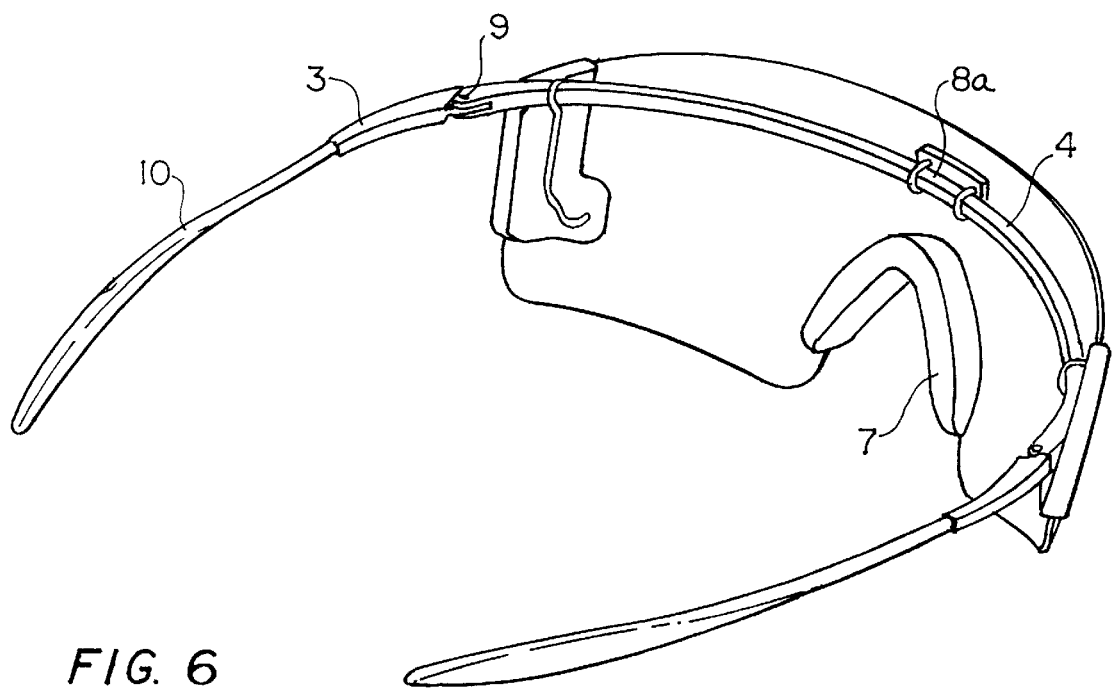
FIG. 6 shows a view of the goggles in FIG. 5 in the operating position.

In the form of embodiment of the goggles shown in FIGS. 5 and 6, the side piece 3 is fixed by the design of the guides 19, especially the area 20 and the joint 8a in the position necessary for both operating and non-operating. The goggles shown in FIGS. 11 to 14 have straight guides 24 for the front piece 4, which have the shape of endpieces that go around the visor 2 on their sides. They are connected to the visor 2 by screw connections 28. The front piece 4 is made of a plastic-coated metal insert 29. The plastic covering 30 is interrupted on the two ends of the front piece 4, in the area where it goes into the end pieces 24. In this area, the metal front piece 4 is connected to the ear piece 5 by a hinge connection 9. The plastic covering 30 is also interrupted in the area of the hinge 25. The metal insert 29 projects into this area between the snap projections 27 of the joint 25. The front piece 4 connected to the ear pieces 5 goes into the recesses 31 of the guides 24 during its up and down folding movements in relation to the visor 2. The guides 24 have surfaces 32 on their sides facing the ear pieces 5 on which the side piece 3 is supported when the goggles are in the operating position, which keep the goggles on the visor 2 from unintentionally folding down. This protects the wearer's face from injury due to the visor 2. The ear pieces 5 also have a safety feature so that the goggles do not unfold in the non-operating position. Each ear piece has a magnet 33 and a small steel plate 34. When the goggles are pressed together, these elements work together and the ear pieces cannot be opened unintentionally.

Figure 9:
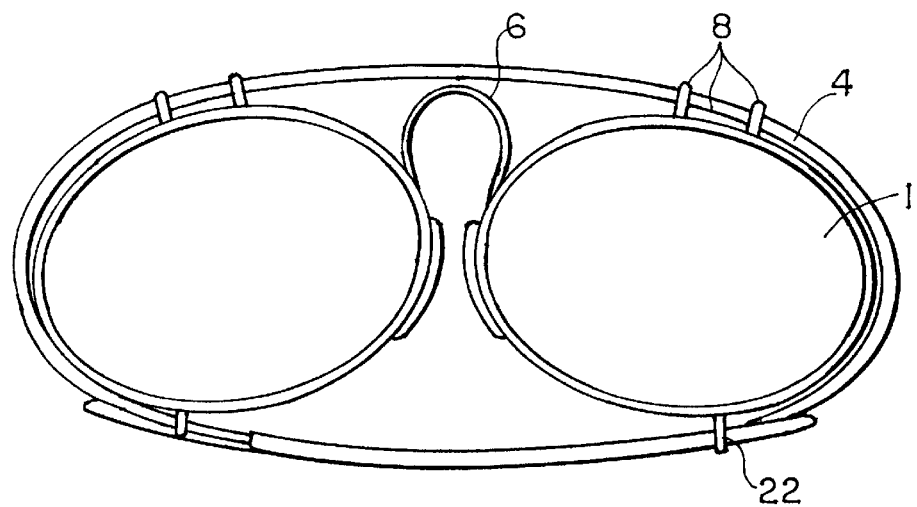
FIG. 9 shows goggles with an elastic bridge in the non-operating position.
Figure 10:
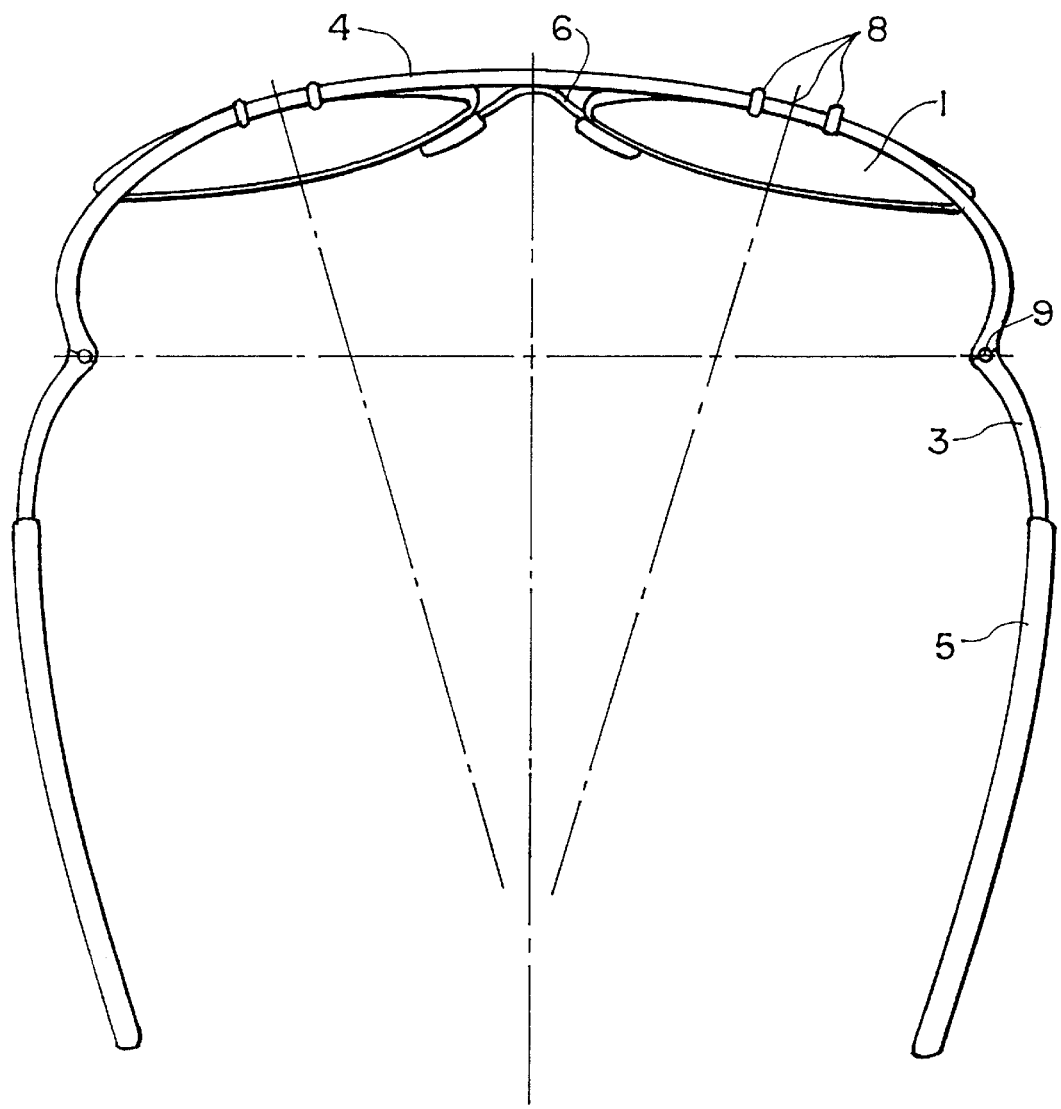
FIG. 10 shows the goggles in FIG. 9 in the operating position.
Figure 11:
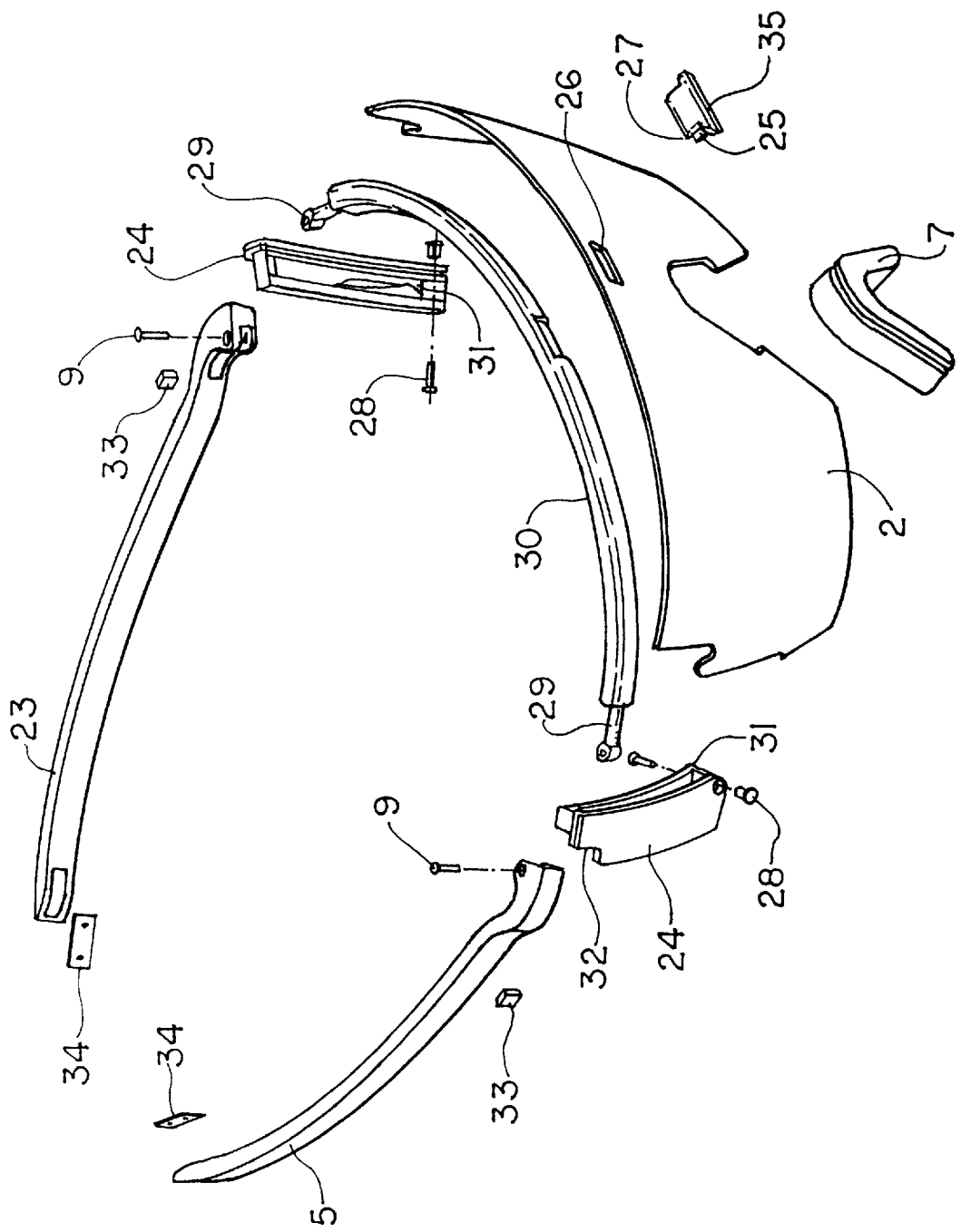
FIG. 11 shows an exploded view of another form of embodiment of the goggles with lateral guides.
Figure 12:
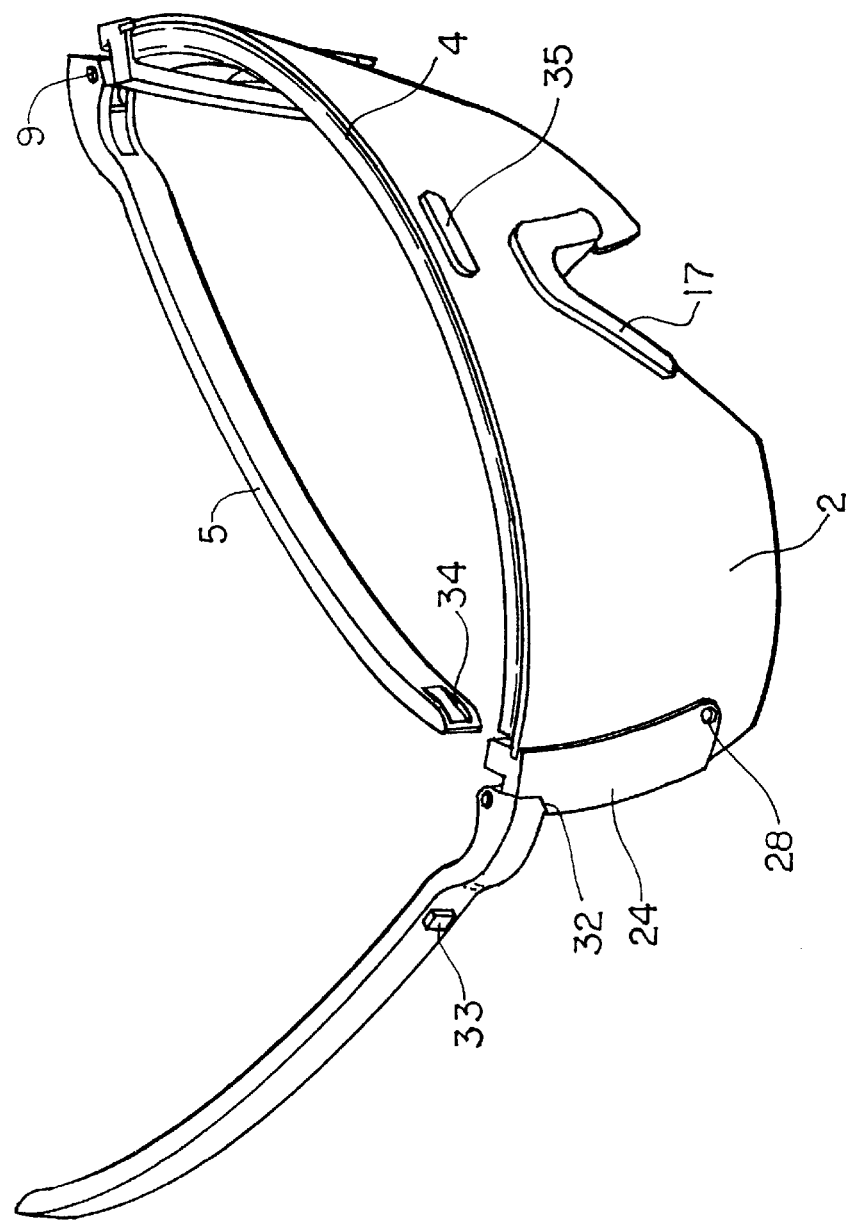
FIG. 12 shows the goggles in FIG. 11 in the operating position.
Figure 13:
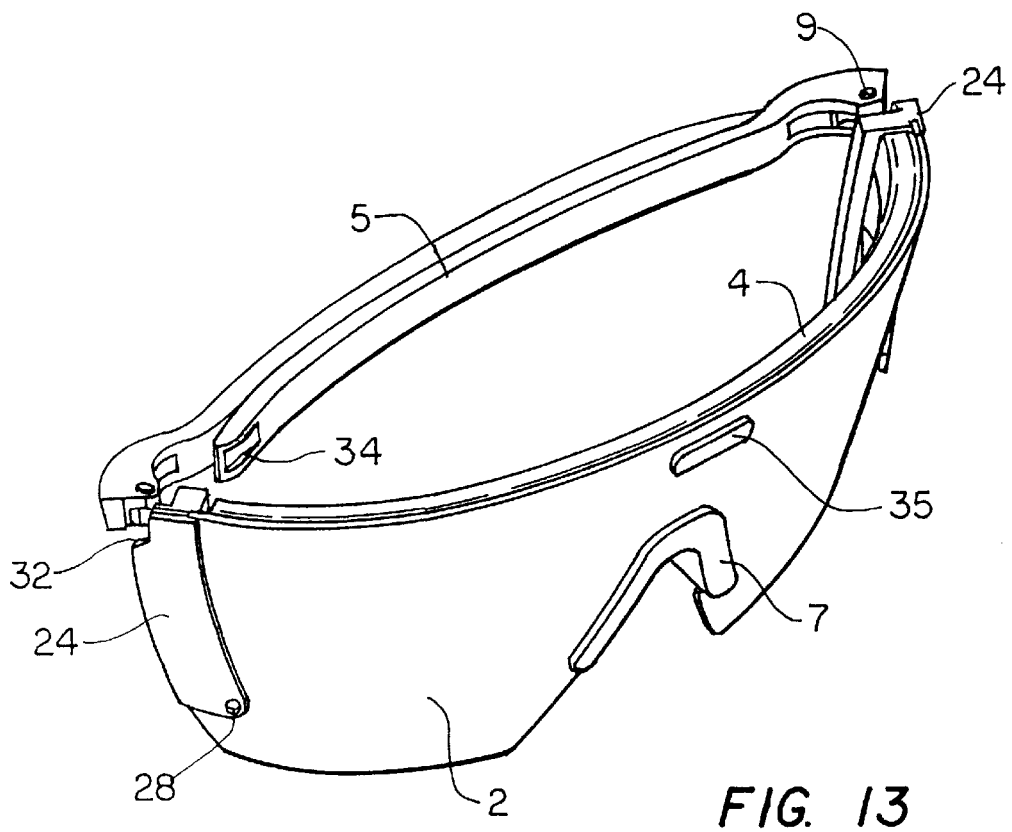
FIG. 13 shows the goggles in FIG. 11 in the semi-closed position.
Figure 14:
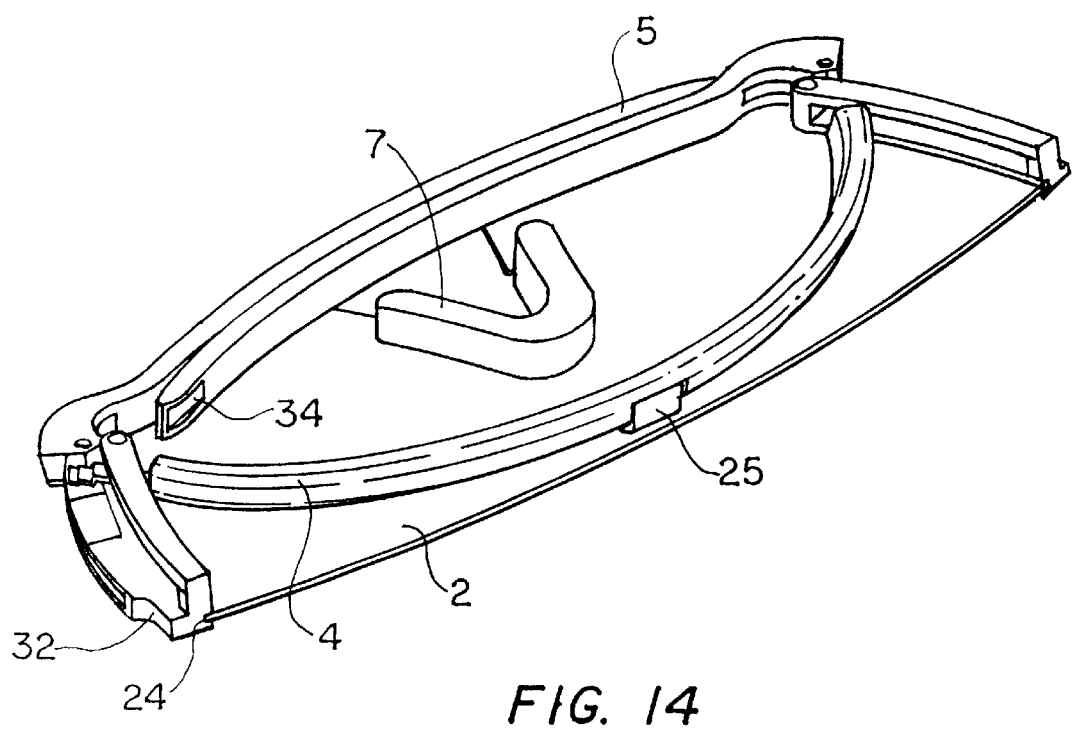
FIG. 14 shows the goggles in FIG. 11 in the non-operating position.

The goggles shown in FIGS. 9 and 10 have stops 22, which fix or support the position of the lenses 1 when the goggles are in the non-operating position by supporting them on the ear pieces 5. Other stops for limiting the folding movement of the lenses are also built into the joints. The pivoting range of the lenses is 90 degrees or less. It corresponds to the inclination. The goggles work as follows: The non-operating position of the goggles is shown in FIGS. 2, 4, 5, 10 and 14. The side piece 3 is on the flat visor 2 (or is in a plane parallel to the visor and 1–2 cm away from it). In the form of embodiment in FIG. 10, the lenses 1 are in the plane of the side piece. They can be surrounded by the side piece 3 when it is folded together. When the ear piece 5 is in the open position, the front piece 4 is basically on the visor 2, and the unfolded ear pieces 5 lie in the same plane as the front piece 4, i.e., they are in a plane lying basically directly on the visor 2. In the form of embodiment in FIG. 10, and the unfolded ear pieces 5 lie in the same plane as the front piece 4 and the lenses 1. In order to put the goggles into the operating position from the non-operating position, the side piece 3 is pivoted in relation to the lenses 1, visor 2 or visor sections. The side piece 3 moves in the direction of the bridge 6, 7. When the ear pieces 5 are unfolded or folded together, the front piece 4 is pivoted in relation to the visor 2; due to the pivot connection 8 or the guides 19, 24, the elastic visor 2 follows the movement of the front piece 4 and is adjusted by its deformation of the curvature. Deformation of the visor 2 and movement of the front piece 4 in relation to the visor 2 continues until the projection 17 snaps into the recess 18 or the front piece 4 reaches the end position of the guides 19, 24. In the form of embodiment shown in FIG. 5, the part up to the front piece 4 is held in the area 20 of the guides 19 by spring-action and interlocking. In this form of embodiment of the goggles (FIGS. 5, 6, 11 to 14), the pivot connection 8a, 25 over the bridge 7 serves as the pivot connection between the side piece 3 and the visor 2,and also takes over the function of supporting the tension mechanics between the front piece 4 and the visor 2. The tensing of the two components against one another and thus the deformation of the elastic element, the visor 2, takes place in this form of embodiment by the working together of the guides 19, 24 and the front piece 4 when the two parts pivot in relation to one another and this movement is basically supported by the pivot connection 8a, 25. In the form of embodiment with two pivoting connections 8, which is arranged on the side of the bridge 7, the front piece 4 is tensed is relation to the visor 2 in such a way that it is adjusted to the curvature of the front piece 4 directly by the tension mechanics formed by the joint connections 8. The pulling and the deforming of the visor 2 is supported by the stops 21a, i.e., a movement of the front piece 4 in its direction of extension is only possible within the sections defined by the distance between the stops 21, 21a; thus, the pulling of the visor 2 and its deformation is defined so that at the given inclination of the visor 2 in relation to the side piece 3, the projection 17 snaps into the recess 18, thus ending the process of opening the goggles. The curvature of the visor 2 in this method of operating the goggles can be changed by pivoting or inclining the side piece plane to the visor plane; by designing the guides 19 appropriately or coordinating the sections defined between the stops 21, 21a and the position of the opening 18 in the visor 2, various curvatures of the visor 2 can be achieved in the operating position with the same front pieces 4 or vice versa. In order to put the form of embodiment of the goggles shown in FIGS. 9 and 10 into the operating position from the non-operating position, the lenses 1 must be pivoted in relation to the side piece 3, so that during the pivoting operation, the elastic bridge 6, which connects the two separate lenses 1 on the front piece 3, is deformed in such a way that the lenses 1 are pivoted away from one another by the spring action of the bridge 6. The elastic bridge 6 makes the lenses 1 go from a position at an angle to one another in the non-operating position of the goggles into a position parallel to one another, which corresponds to the operating position of the goggles.

To put the goggles into the folded position from the open or operating position, the operations are performed in reverse order. To fold the goggles shown in FIGS. 2, 3 and 4 together, first light pressure is necessary on the projection 17 against the visor 2 in order to push it out of the hole 18, since otherwise the front piece 4 cannot pivot in relation to the visor 2. If the projection 17 is removed from the hole 18, the two components can be pivoted in relation to one another, the curvature of the visor 2 is eliminated and it goes back to its original flat form. The front piece 4 lies on the flat visor 2. The ear pieces 5, which advantageously have no offsets on the ear, are now folded together, so that in one advantageous form of embodiment of the goggles, the whole side piece 3 lies in the contour area of the visor. The height of the goggles in the invention in this state is roughly 0.8–9 mm. In the form of embodiment shown in FIGS. 5, 6 and 11 to 14, in order to put the goggles from the operating into the non-operating position, light pressure must be exerted on the opened side piece 3 while simultaneously holding the visor 2 fixed, advantageously in the area of the pivoting connection 8a, 25, so that the tension between the curved visor 2 and the front piece 4 is released. The further movement of the front piece 4 into the guides 19, 24 takes place almost by itself, since the tension between the two components is released and the goggles try to go into a state free of tension. This movement takes place until the visor 2 has assumed its flat form. The last operation of the goggles is thus ended. In the form of embodiment of the goggles shown in FIGS. 9 and 10, light pressure on the visor 1 deforms the elastic bridge 6 and causes an angular position of the lenses in relation to one another, so that they go into the plane of the side piece. When the goggles are opened, they go into the opening operation by just slightly touching the visor 1, since the elastic bridge 6 is under tension and supports the opening movement. In the forms of embodiment of the goggles shown in FIGS. 1 to 6, the components (side piece 3 and visor 2) are tensed in relation to one another in the operating position.

I claim:

1. Goggles, comprising:
   a side piece, a curved front piece and at least one visor section having a bridge for a nose, wherein the side piece and the at least one visor section can pivot in relation to one another and the side piece and the at least one visor section are in different planes in an operating position, standing at an angle to one another and are in planes lying substantially parallel to one another in a non-operating position, characterized by the fact that the at least one visor section is elastic and is connected to the side piece via joining structures so that when the side piece is pivoted in relation to the at least one visor section, the at least one visor section is deformed elastically and adjusted to the approximate curvature of the front piece.

2. Goggles according to claim 1, wherein the visor sections are connected to one another by means of a deformable bridge or pad for the nose.

3. Goggles according to claim 1, wherein deformation of the at least one visor section can be changed by pivoting the front piece.

4. Goggles according to claim 1, wherein the joining structures are formed by loops disposed around the front piece and are arranged on the at least one visor section and wherein the at least one visor section in the area of the joining structures are positioned by stops arranged on the front piece.

5. Goggles according to claim 1, wherein the joining structures are formed by pegs that are insertable into recesses in the visor on the front piece.

6. Goggles according to claim 1, including means of positioning the side piece in relation to the at least one visor section.

7. Goggles according to claim 6, wherein the means of positioning are formed by a snap connection between the front piece and the visor, whereby a projection of the front piece is insertable into a recess on a section including the at least one visor section and the nose bridge.

8. Goggles according to claim 1, wherein when the at least one visor section is connected to the front piece via lateral guides, there is a pivot connection in the middle of the visor or bridge.

9. Goggles according to claim 8, wherein positioning is accomplished with guides arranged on the outer edge of the at least one visor section by spring-action or interlocking between the guide and the front piece in the operating position in the area.

10. Goggles according to claim 1, wherein the at least one visor section and the side piece can be separated in their pivot connection.

11. Goggles according to claim 4, wherein the loops are open in one sub-area and release the side piece when turned 90 degrees and thus allow the at least one visor section to be separated from the front piece.

12. Goggles according to claim 4, wherein the loops are closed and thereby completely surround the front piece and are connected to the at least one visor section so that such can be detached.

13. Goggles according to claim 10, wherein the joining structure arranged in the middle can snap the visor and has two snap projections on the side facing inward which hold the front piece between them by means of a snap connection.

14. Goggles according to claim 13, wherein the front piece includes a plastic-covered metal core.

15. Goggles according to claim 9, wherein the guides are end pieces surrounding the visor on the side, which have a surface, on which the side piece is supported and positioned when the goggles are in the open position.

16. Goggles, comprising: a side piece, a curved front piece and visors that have an elastically deformable nose bridge therebetween, wherein the side piece and the visors can be pivoted in relation to one another and the side piece and the visors in an operating position lie in different planes at an angle to one another and in a non-operating position lie in planes substantially parallel to one another, wherein the visors are disposed on the front piece with hinge members and the visors are connected to one another via the elastically deformable nose bridge that is under tension in the non-operating position and wherein the pivoting of the side piece in relation to the visor causes the elastic deformation of the bridge and thus the movement of the visor into the operating position.

17. Goggles according to claim 16, wherein the side piece is thin and is composed of a wire-shaped material.

18. Goggles according to claim 16, wherein the side piece and its front piece have stops as positioning aids to position the side piece of the goggles in relation to the visor in the non-operating position of the goggles.

19. Goggles according to claim 16, wherein the side piece is secured against opening in the closed state.

* * * * *